United States Patent
Lewis et al.

(10) Patent No.: US 10,203,058 B2
(45) Date of Patent: Feb. 12, 2019

(54) REVERSE BARB FLUID CONNECTOR AND METHOD OF FLUID CONNECTION

(71) Applicant: Nordson Corporation, Westlake, OH (US)

(72) Inventors: Peter D. Lewis, Fort Collins, CO (US); Kyle R. Steele, Windsor, CO (US)

(73) Assignee: Nordson Corporation, Westlake, OH (US)

( * ) Notice: Subject to any disclaimer, the term of this patent is extended or adjusted under 35 U.S.C. 154(b) by 285 days.

(21) Appl. No.: 14/693,238

(22) Filed: Apr. 22, 2015

(65) Prior Publication Data

US 2015/0308598 A1     Oct. 29, 2015

Related U.S. Application Data

(60) Provisional application No. 61/983,701, filed on Apr. 24, 2014.

(51) Int. Cl.
*F16L 33/23*     (2006.01)
*A61M 39/10*     (2006.01)
*A61M 39/12*     (2006.01)

(52) U.S. Cl.
CPC .......... *F16L 33/23* (2013.01); *A61M 39/1011* (2013.01); *A61M 39/12* (2013.01); *F16L 2201/44* (2013.01)

(58) Field of Classification Search
CPC ......... F16L 33/23; F16L 33/035; F16L 33/12; F16L 33/223; F16L 2201/44; F16L 23/06; A61M 39/12; Y10T 24/1418
See application file for complete search history.

(56) References Cited

U.S. PATENT DOCUMENTS

| | | | | |
|---|---|---|---|---|
| 1,646,463 | A | * | 10/1927 | Stokesberry ............ F16L 23/06 24/273 |
| 2,147,355 | A | | 2/1939 | Scholtes |
| 3,272,536 | A | * | 9/1966 | Weinhold ................ F16L 33/12 285/114 |
| 3,476,410 | A | * | 11/1969 | Pastva, Jr. ............... F16L 17/04 24/270 |
| 4,473,369 | A | | 9/1984 | Lueders et al. |
| 4,631,056 | A | | 12/1986 | Dye |
| 4,723,948 | A | | 2/1988 | Clark et al. |
| | | | (Continued) | |

FOREIGN PATENT DOCUMENTS

| | | | | | |
|---|---|---|---|---|---|
| CH | | 405838 A | * | 1/1966 | .............. F16L 14/04 |
| DE | | 1245656 B | * | 7/1967 | ............ F16L 17/067 |
| | | (Continued) | | | |

*Primary Examiner* — David Bochna
*Assistant Examiner* — James A Linford
(74) *Attorney, Agent, or Firm* — Baker & Hostetler LLP

(57) ABSTRACT

A fluid connector includes first and second clamping arms coupled together for movement between an open condition and a closed, clamping condition for clamping an end of a length of flexible tubing to a fluid fitting. The first and second clamping arms each have a curved interior surface and at least one barb on each curved interior surface. The barbs are configured to engage the exterior surface of the flexible tubing when the first and second clamping arms are in the closed, clamping condition to form a fluid tight connection between the fluid fitting and the flexible tubing. A fluid system and method of fluid connection using the fluid connector are also disclosed.

19 Claims, 11 Drawing Sheets

(56) References Cited

U.S. PATENT DOCUMENTS

| | | |
|---|---|---|
| 5,074,600 A | 12/1991 | Weinhold |
| 5,797,633 A | 8/1998 | Katzer et al. |
| 5,884,943 A | 3/1999 | Katzer et al. |
| 6,155,610 A | 12/2000 | Godeau et al. |
| 6,913,294 B2 | 7/2005 | Treverton et al. |
| 7,125,056 B2 | 10/2006 | Saarem |
| 8,177,771 B2 | 5/2012 | Butts et al. |
| 8,297,661 B2 | 10/2012 | Proulx et al. |
| 2008/0221469 A1 | 9/2008 | Shevchuk |
| 2012/0299296 A1 | 11/2012 | Lombardi, III |

FOREIGN PATENT DOCUMENTS

| | | | |
|---|---|---|---|
| DE | 3046170 A1 * | 7/1982 | ............ F16L 23/06 |
| DE | 3133837 A1 | 3/1983 | |
| DE | 4433812 A1 | 3/1996 | |
| EP | 1788292 A2 | 5/2007 | |
| FR | 2645616 A1 | 10/1990 | |
| WO | 2013076153 A1 | 5/2013 | |

\* cited by examiner

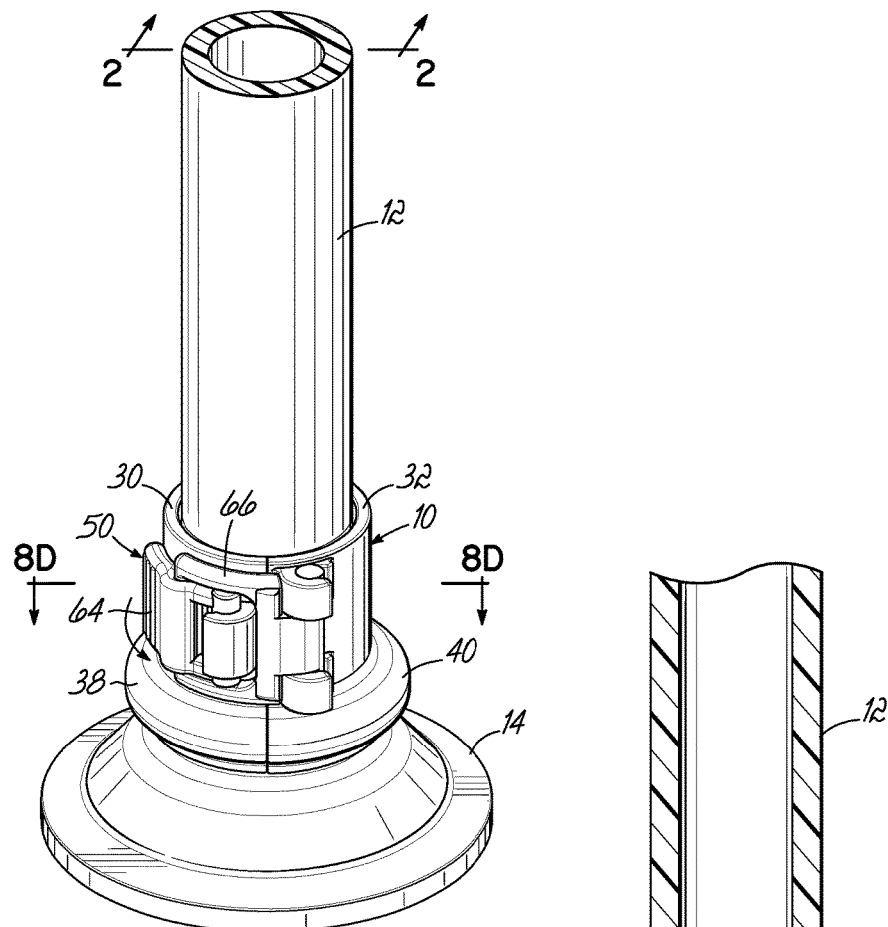
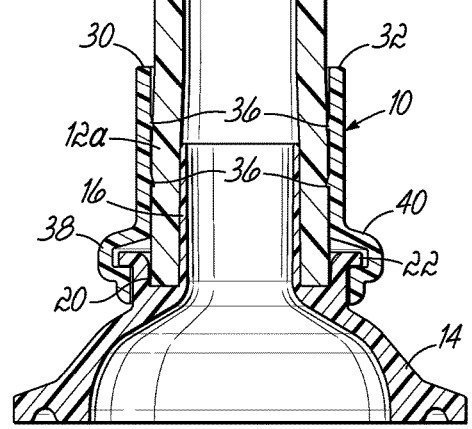
FIG. 1
FIG. 2

REVERSE BARB FLUID CONNECTOR AND METHOD OF FLUID CONNECTION

CROSS-REFERENCE TO RELATED APPLICATION

This application claims the benefit of U.S. Provisional Patent Application No. 61/983,701, filed on Apr. 24, 2014 (pending), the disclosure of which is incorporated by reference herein in its entirety.

TECHNICAL FIELD

The present invention generally relates to fluid connectors and, more specifically to barbed fluid connectors.

BACKGROUND

Traditional barbed fluid connectors seal on the interior surface of a piece of flexible tubing. This presents various challenges or problems. For example, such a construction can present a location for trapping the fluid under the barb or barbs, and causing contamination of the fluid system. It can also be difficult inserting the end of the flexible tubing over the barbed end of a connector, especially with larger diameter tubing. Finally, the inner diameter of the barbed connector is typically smaller than the inner diameter of the flexible tubing. Therefore, the barbed connector can present an undesirable restriction in fluid flow.

SUMMARY

In an illustrative embodiment, the invention provides a fluid connector comprising first and second curved clamping portions coupled together for movement between an open condition and a closed, clamping condition for clamping an end of a length of flexible tubing to a fluid fitting. The first and second clamping portions each have a curved interior surface and at least one barb on each curved interior surface. The barbs are configured to engage the exterior surface of the flexible tubing when the first and second clamping portions are in the closed, clamping condition to form a fluid tight connection between the fluid fitting and the flexible tubing.

In another embodiment, a fluid system comprises first and second clamping portions coupled together for movement between an open condition and a closed, clamping condition. The first and second clamping portions each have a curved interior surface and at least one barb on each curved interior surface. The system further includes a length of flexible tubing, and a fluid fitting configured to receive an end of the length of flexible tubing. The barbs of the first and second clamping portions engage the exterior surface of the flexible tubing when the first and second clamping portions are in the closed, clamping condition to form a fluid tight connection between the fluid fitting and the flexible tubing.

In another aspect, a method of forming a fluid tight connection between a length of flexible tubing and a fluid fitting includes directing the end of a length of flexible tubing over a fluid fitting to form fluid passage communicating from the flexible tubing through the fluid fitting. A fluid connector is placed around the end of the length of flexible tubing. The first and second clamping portions of the fluid connector are moved into a clamping condition onto the exterior surface of the flexible tubing. At least one barb on an interior surface of the first and second clamping portions engages into the exterior surface of the flexible tubing when the fluid connector is in the clamping condition to thereby form a fluid tight connection between the flexible tubing and the fluid fitting.

Various additional features and advantages will become readily apparent to those of ordinary skill in the art upon review of the following detailed description of the illustrative embodiments, taken in conjunction with the accompanying drawings.

BRIEF DESCRIPTION OF THE DRAWINGS

FIG. 1 is a perspective view of an illustrative embodiment of a fluid connector in accordance with an illustrative embodiment of the invention coupled to a length of flexible tubing.

FIG. 2 is a cross sectional view taken along line 2-2 of FIG. 1.

DETAILED DESCRIPTION

Figure 3:
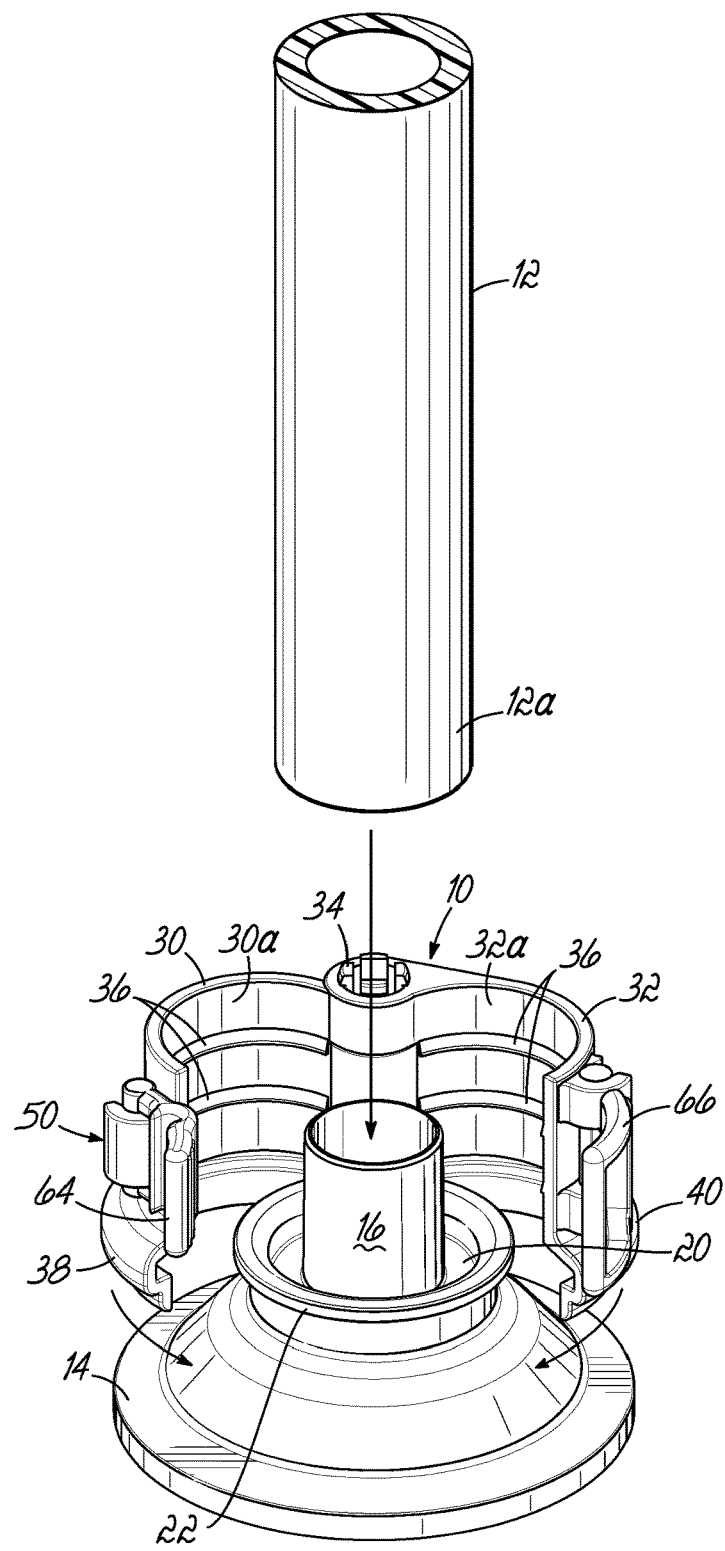
FIG. 3 is a disassembled perspective view of the connector and tubing of FIG. 1.

An illustrative embodiment of a fluid connector 10 for medical, biopharma or other fluid connection applications is shown in FIGS. 1 and 2. The connector 10 may be made from any suitable material, such as medical grade polymer(s). FIG. 1 illustrates an assembly including the connector 10 used for coupling a length of flexible tubing 12, such as resilient silicone tubing, to a fluid fitting such as a sanitary fitting 14. The connector 10, tubing 12 and fitting 14 comprise a fluid system, although it will be understood that such as system may comprise further components and fluid components having a wide variety of designs and uses. As shown in more detail in the cross sectional view of FIG. 2, the end 12a of the medical tubing 12 is placed over a more rigid cylindrical extension 16 of the sanitary fitting 14 and within a shallow annular recess 20. The end 12a may be received on the extension 16 with a friction fit or more loosely, depending on the applied clamping force of the connector 10. The recess 20 is formed between the cylindrical extension 16 and an upstanding annular flange 22. The connector 10 is formed with two clamp arms 30, 32 coupled together by a hinge or pivot 34 (FIG. 3). As further shown best in FIG. 3, the semi-cylindrical inner surfaces 30a, 32a of the clamp arms 30, 32 include barbs 36. Each clamp arm 30, 32 include a shroud 38, 40 that secures onto the flange 22 of the sanitary fitting 14. The shrouds 38, 40 increase the pull off force of the tubing 12 and allow any pulling force on the tubing 12 to be spread away from the hinge or pivot 34 to reduce the likelihood that the hinge or pivot 34 will deform or fracture under such force. As discussed further below, the connector 10 includes a suitable coupling element for securing the clamp arms 30, 32 around the tubing 12 as shown in FIG. 1. In the illustrative embodiment shown, the coupling element is an over center clasp mechanism 50. When the clamp arms 30, 32 are clamped around the end 12a of the medical tubing 12, the barbs 36 bite into the tubing 12 as shown best in FIG. 2. This forms a fluid tight connection between the end 12a of the tubing 12 and the cylindrical extension 16 of the sanitary fitting 14. The sanitary fitting 14 may be a fluid fitting of any suitable design, other than that shown in the illustrative embodiment. Such sanitary fittings are designed to mate with other sanitary fittings using a gasket and a clamp (not shown). It will be understood that aspects and features of the present invention may be used to facilitate fluid tight connections between lengths of tubing and other types of fittings, such as fittings on other fluid components, or even fittings to connect other lengths of tubing. Although two barbs 36 are shown on the interior surface of each clamp arm 30, 32, only one barb 36 may be provided on each clamp arm 30, 32 depending on the application, and there may be other applications in which more than two barbs 36 are desired or necessary. The use an over center clasp mechanism 50, such as the one illustrated in the drawings, provides mechanical advantage when clamping and locking the clamp arms 30, 32 onto the outer surface of the tubing 12. In this manner, the user is able to apply significant clamping force with reduced effort.

Figure 4:
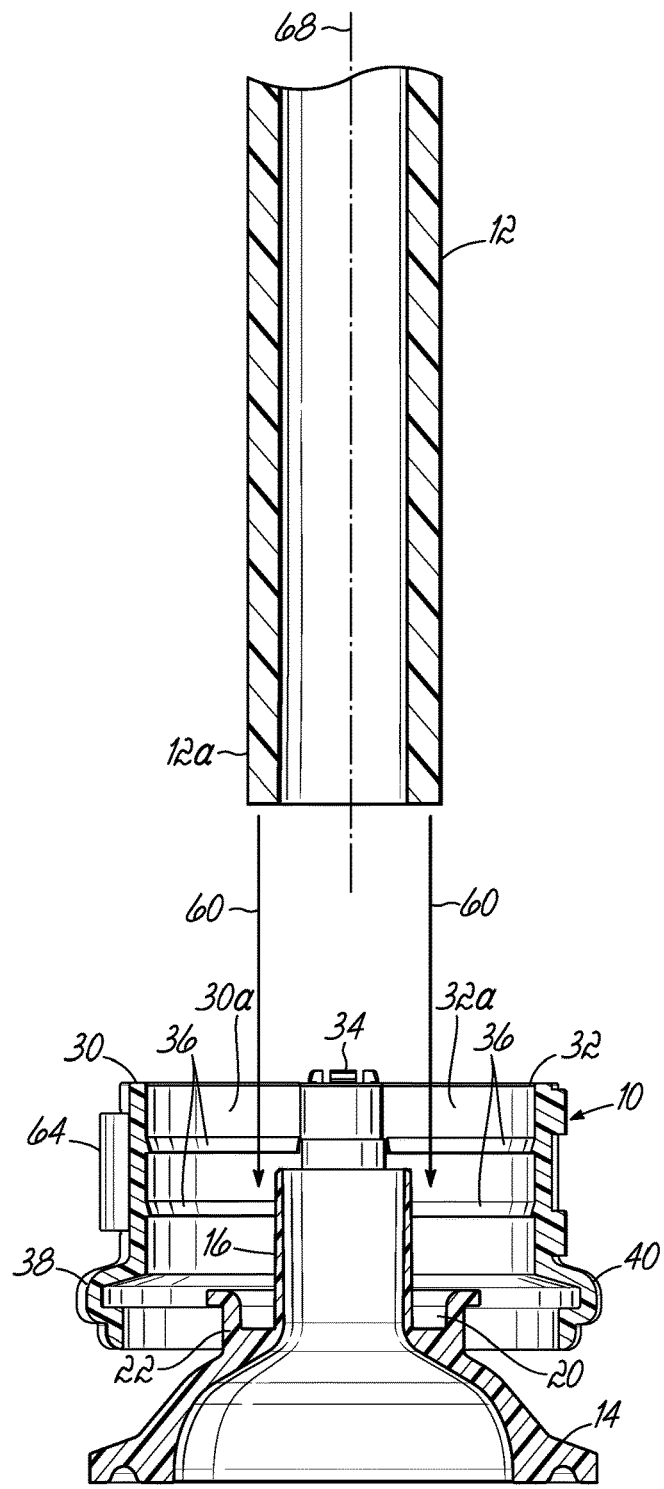
FIG. 4 is a lengthwise axial cross sectional view of the assembly shown in FIG. 3.
Figures 5, 6:
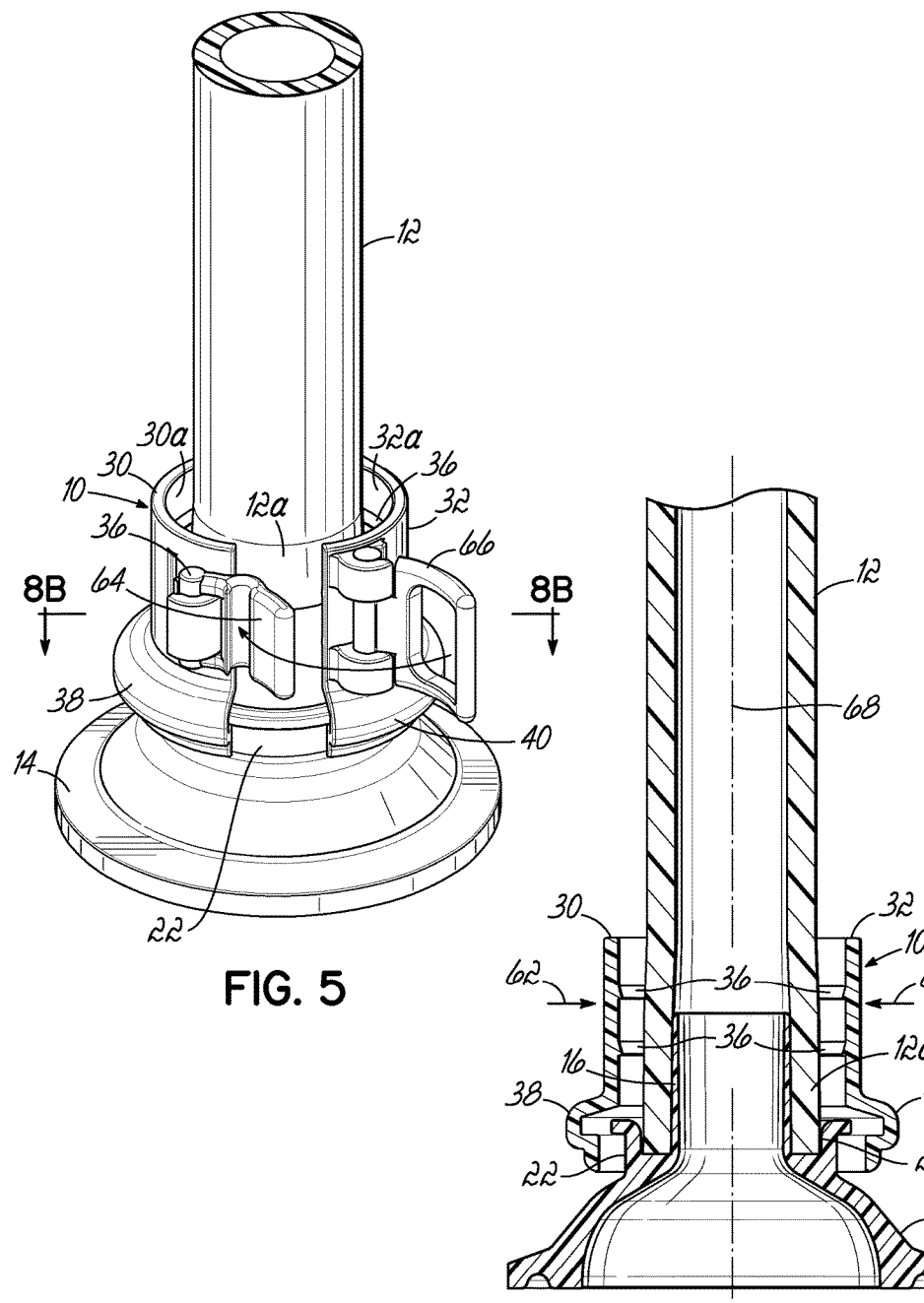
FIG. 5 is a perspective view similar to FIG. 1, but showing the connector in an open condition.
FIG. 6 is a lengthwise axial cross sectional view of the assembly shown in FIG. 5.
Figure 7:
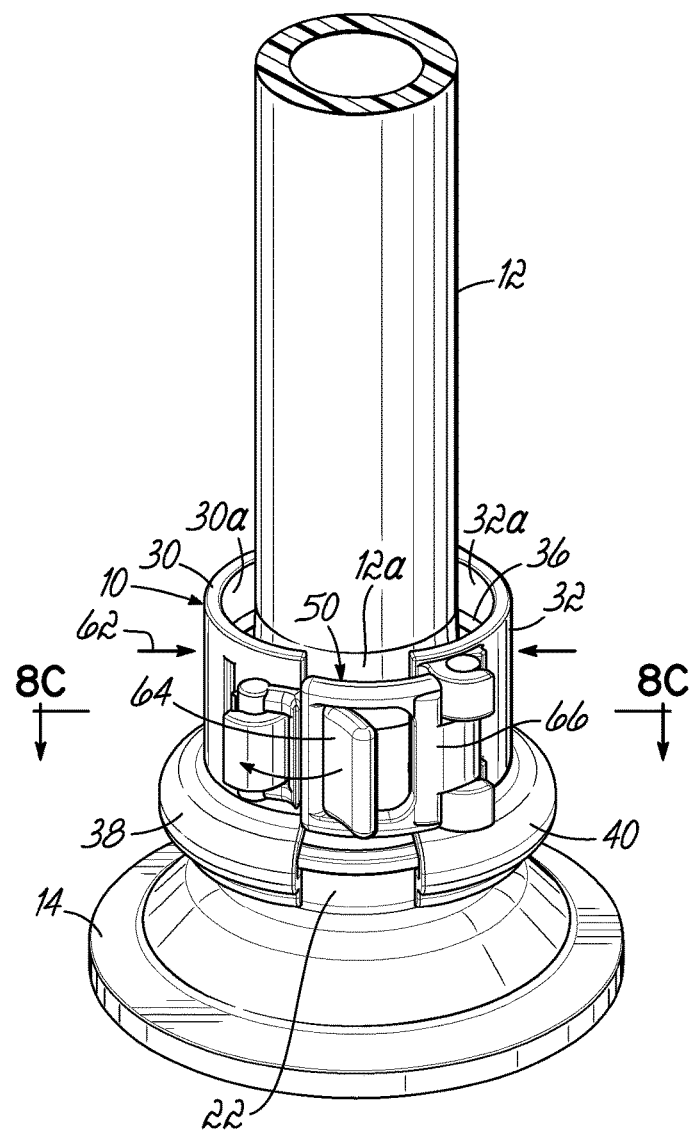
FIG. 7 is a perspective view similar to FIG. 5, but showing the connector in the process of being clamped onto the tubing and an underlying fluid fitting.

FIGS. 4-7 illustrate a procedure for coupling a length of resilient medical tubing 12, such as silicone tubing, to a sanitary fitting 14 using a reverse barb connector 10. As shown in FIG. 4, the end 12a of the tubing 12 is directed over the extension 16 as shown by the arrows 60. Once the end 12a of the tubing 12 is received by the extension 16 as shown in FIGS. 5 and 6, the connector 10 is opened and placed around the end 12a of the tubing 12 as well as the extension 16 and annular flange 22 in the position shown. The two clamp arms 30, 32 are pivoted toward one another as shown by the arrows 62 in FIG. 6. The annular flange 22 is received by the semi-annular shrouds 38, 40 of each clamp arm 30, 32 as shown in FIGS. 6 and 7. As further shown in FIG. 7, a pivotal clasp element 64 coupled with one of the clamp arms 30 is directed through a buckle element 66 pivotally coupled with the other clamp arm 32. The components 64, 66 of the clamp mechanism 50 rotate about axes that are at least generally parallel to the longitudinal axis 68 of the tubing 12 (see FIGS. 4 and 6).

Figure 8A:
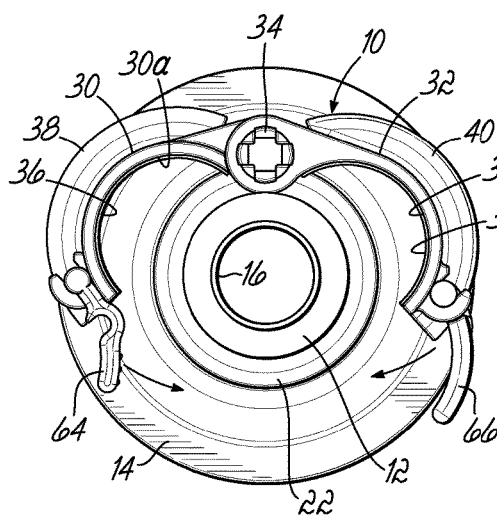
FIG. 8A is a top view of the assembly shown in FIG. 3.
Figure 8B:
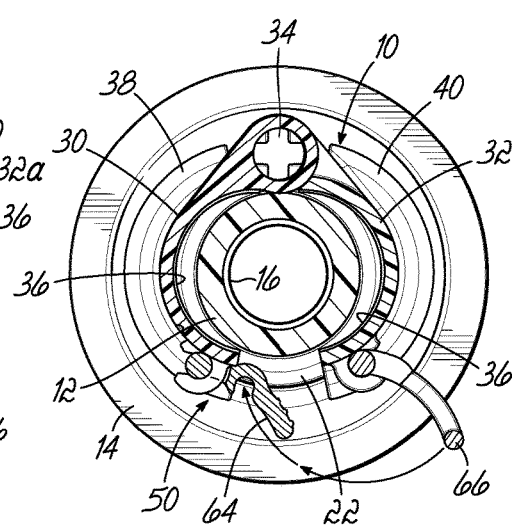
FIG. 8B is a cross sectional view taken along line 8B-8B of FIG. 5.
Figure 8C:
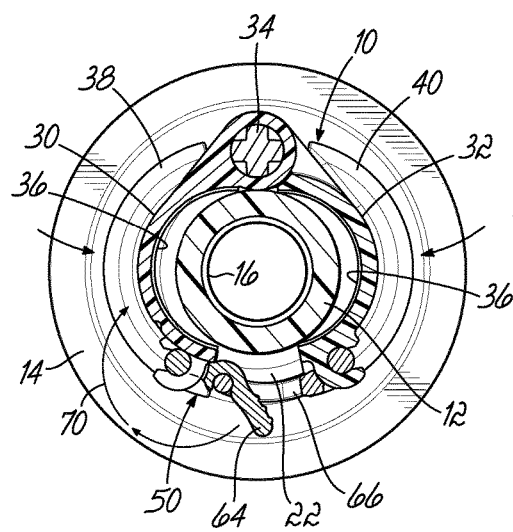
FIG. 8C is a cross sectional view taken along line 8C-8C of FIG. 7.
Figure 8D:
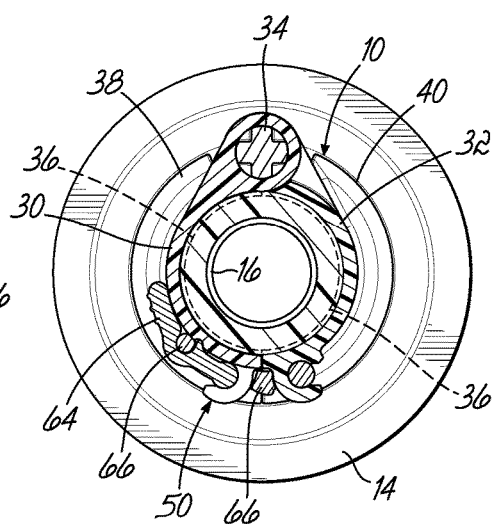
FIG. 8D is a cross sectional view taken along line 8D-8D of FIG. 1.

The connection method is also illustrated in FIGS. 8A-8D. FIG. 8A corresponds generally to the open condition of the connector 10 shown in FIG. 4 prior to receiving the tubing 12. FIG. 8B corresponds generally to the condition to the connector 10 as shown in FIG. 5 with the tubing 12 in place on the extension 16 of the sanitary fitting 14 and the clamp arms 30, 32 being brought together around the tubing 12 as well as the connecting portion of the sanitary fitting 14. FIG. 8C illustrates the point in the method of coupling during which the clasp element 64 is directed through the buckle element 66 and the direction of rotation initiated by the user, and shown by the arrows 70, for bringing the clamp arms 30,32 together with an over center mechanical advantage. FIG. 8D then illustrates the final position of the clasp element 64 locked into place with the clamp arms 30, 32 firmly engaging the exterior surface of the tubing 12 and the barbs 36 biting into that exterior surface of the tubing 12 as illustrated by the dashed lines.

Figure 9:
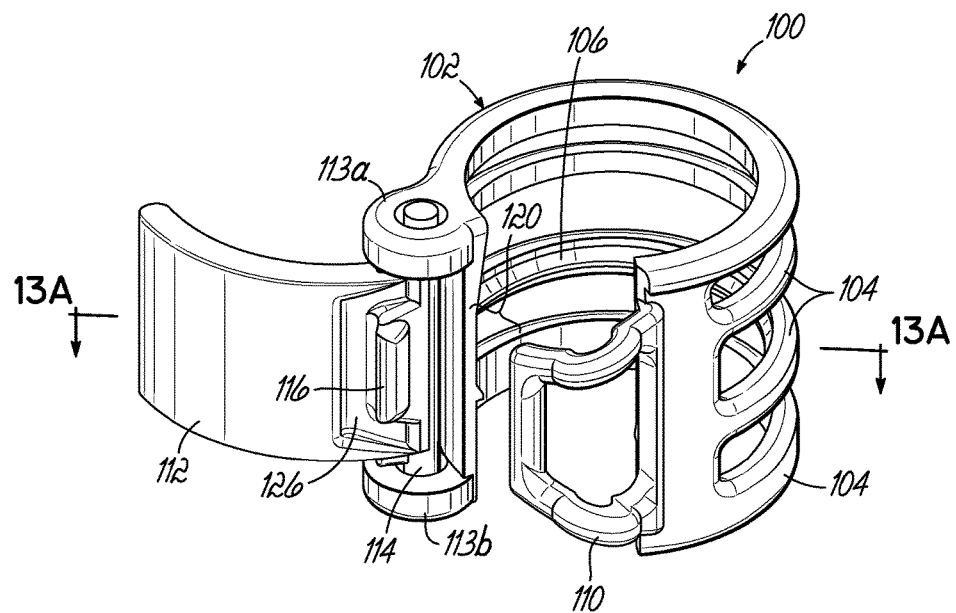
FIG. 9 is a perspective view of another illustrative embodiment of a fluid connector according to the invention.
Figure 10:
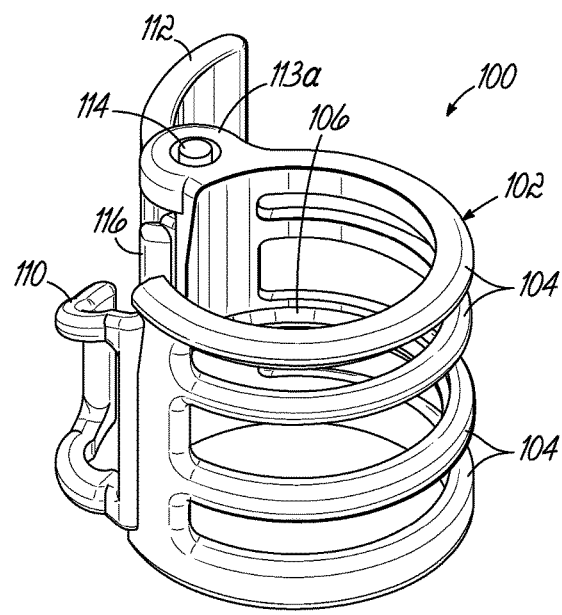
FIG. 10 is a perspective view of the connector illustrated in FIG. 9, but with the connector rotated approximately 90°.
Figure 11A:
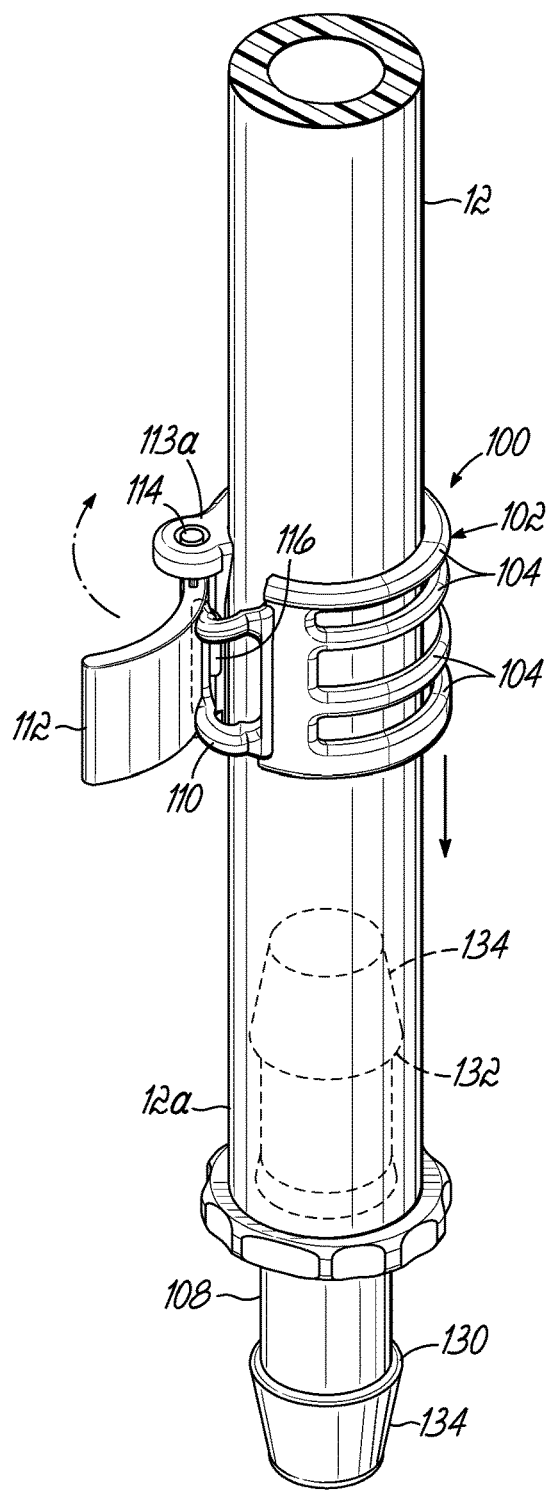
FIG. 11A is a perspective view illustrating the fluid connector of FIG. 9 assembled to a length of tubing and being coupled with a barbed fluid fitting.
Figure 11B:
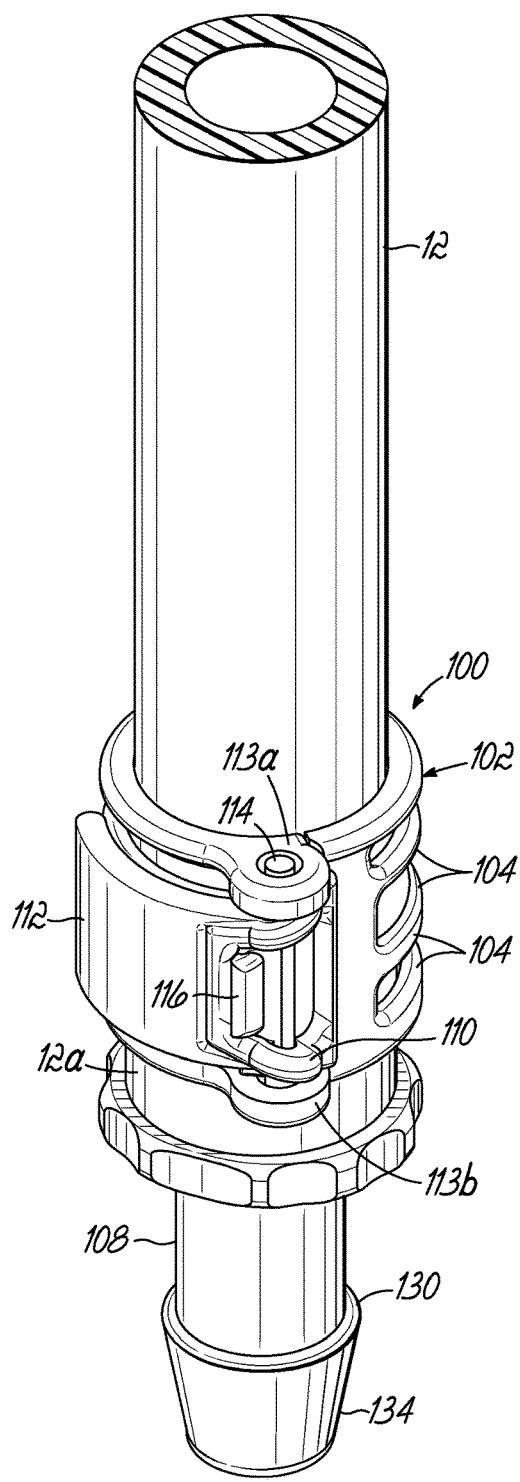
FIG. 11B is a perspective view similar to FIG. 11A but illustrating the fluid connector in the closed or clamped condition on the tubing and fluid fitting.
Figure 12:
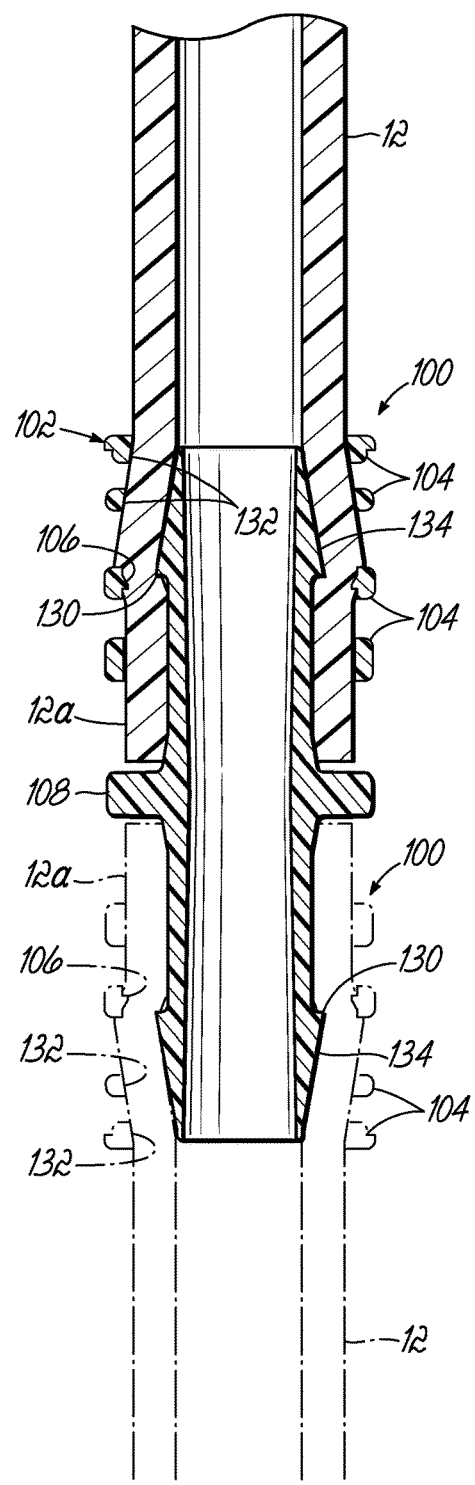
FIG. 12 is a lengthwise axial cross sectional view of the assembled tubing, connector, and fluid fitting shown in FIG. 11B.
Figure 13A:
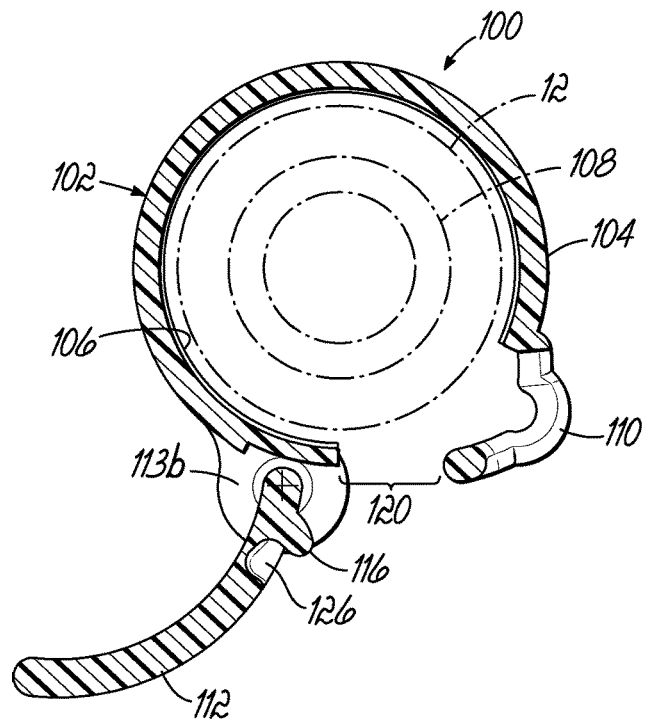
FIG. 13A is a cross sectional view taken along line 13A-13A of FIG. 9.
Figure 13B:
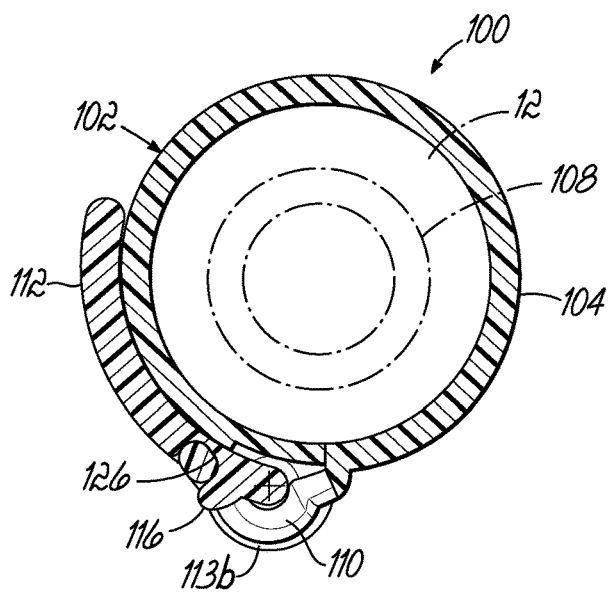
FIG. 13B is a cross sectional view similar to FIG. 13A, but illustrating the latched or closed condition of the connector.

Another alternative embodiment is illustrating in FIG. 9 through 13B. As generally illustrated in FIGS. 9 and 10, a reverse barb fluid connector 100 in this embodiment includes a one piece clamping body 102 that has a generally cylindrical cage-type structure. Clamping members 104 are spaced apart along the body 102 and at least one of these clamping members 104 includes a barb 106 similar to the barbs 36 shown and described with regard to the first embodiment. The connector 100 may be used to connect conventional silicone medical tubing 12 to a conventional barbed sanitary fitting 108. The connector body 102 is preferably formed from a flexible medical grade polymeric material, such as USP Class 6 glass-filled Nylon, or USP Class 6 polypropylene and is flexible enough such that it may be flexed opened and placed around an existing fluid fitting/tubing assembly as shown best in FIG. 12. As with the first embodiment the fluid fitting 108 and the tubing 12 may remain attached to each other as the connector 100 is clamped into place thereby maintaining sterility and fluid integrity of the system. Referring to FIGS. 9, 10, 11A and 11B, the connector 100 is formed with a buckle connector 110 integrally molded with the body 102, and a pivoting clasp 112. The clasp 112 has a pin 114 at one end and an attached latch member 116 that couples with the buckle connector 110. An opening 120 is located between pin receiving elements 113a, 113b and the buckle connector 110 for receiving the tubing 12 during assembly. The buckle connector 110 has an over center movement as best illustrated in FIGS. 13A and 13B. The connector body 102 may be flexed such that the opening 120 is large enough to receive the tubing 12 when it is already coupled to the underlying fluid fitting 108. This results in the assembly as shown in FIG. 13A. Then, the buckle connector 110 is coupled or placed into a groove 126 of the clasp 112 and the clasp 112 is pivoted to the position shown in FIG. 13B with the action of an over center buckle assembly. This results in the clamped, fluid tight assembly shown in FIG. 12 with the reverse barb element or elements 106 forced into the resilient tubing material 12 at the tube end 12a, at least proximate to the barbed edge 130 of the fluid fitting 108. In addition, the tubing 12 is prevented from ballooning or bulging radially outward at the edge of the connector 100 because the fluid body internal diameter has a tapered inner surface 132 generally corresponding to the taper of the fluid fitting outer surface 134. Thus, the inner surfaces 132 of the fluid connector body 102 are maintained generally parallel to the outer tapered surface 134 of a standard, barbed fluid fitting, as shown in FIG. 12.

While the present invention has been illustrated by the description of one or more embodiments thereof, and while the embodiments have been described in considerable detail, they are not intended to restrict or in any way limit the scope of the appended claims to such detail. The various features as described herein may be used in the described combinations or in any combination according to the needs of the user. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

What is claimed is:

1. A fluid connector for securing a length of flexible tubing to a fluid fitting that includes a flange, the fluid connector comprising:
    first and second clamping portions coupled together for movement between an open condition and a closed, clamping condition for clamping an end of a length of flexible tubing to a fluid fitting, wherein each of the first and second clamping portions defines an upper portion and a lower portion opposite the upper portion,
    the first and second clamping portions each having an outer surface, a curved interior surface opposite the outer surface, and at least one barb extending radially from each curved interior surface at the upper portion, the at least one barb configured to engage an exterior surface of the flexible tubing when the first and second clamping portions are in the closed, clamping condition to form a fluid tight connection between the fluid fitting and the flexible tubing, the lower portion of the first and second clamping portions each including a shroud that defines a recess, wherein the recess is configured to receive the flange of the fluid fitting,
    wherein when the first and second clamping portions are in the closed, clamping condition, the fluid connector has 1) a first diameter measured from a location on the curved interior surface at the upper portion of the first clamping portion that is spaced from the at least one barb of the first clamping portion to the curved interior surface of the second clamping portion, 2) a second diameter measured from an inner surface of the shroud of the first clamping portion to an inner surface of the shroud of the second clamping portion, and 3) a third diameter measured from the outer surface of the first clamping portion to the outer surface of the second clamping portion, wherein the second diameter is greater than the first and third diameters.

2. The fluid connector of claim 1, wherein the first and second clamping portions further comprise first and second clamping arms pivotally coupled to each other.

3. The fluid connector of claim 1, further comprising an over center clasp mechanism configured to couple the first and second clamping portions together.

4. The fluid connector of claim 1, wherein when the first and second clamping portions are in the closed, clamping condition, the upper portions of the first and second clamping portion collectively define a first cylindrical portion of the fluid connector, and the lower portions of the first and second clamping portion collectively define a second cylindrical portion and a conical portion of the fluid connector.

5. The fluid connector of claim 4, wherein the conical portion of the fluid connecter has a fourth diameter measured from the outer surface of the first clamping portion to the outer surface of the second clamping portion, wherein the fourth diameter is greater than the first, second, and third diameters.

6. The fluid connector of claim 5, wherein the conical portion of the fluid connector is spaced between the first and second cylindrical portions of the fluid connector.

7. The fluid connector of claim 6, wherein the second cylindrical portion of the fluid connector has a fifth diameter measured from the outer surface of the first clamping portion to the outer surface of the second clamping portion, wherein the fifth diameter is greater than the first and third diameters and less than the second and fourth diameters.

8. The fluid connector of claim 7, wherein the second cylindrical portion of the fluid connector has a sixth diameter measured from the inner surface of the first clamping portion to the inner surface of the second clamping portion, wherein the sixth diameter is greater than the first and third diameters and less than the second, fourth, and fifth diameters.

9. A fluid system, comprising:
    a fluid connector comprising first and second clamping portions coupled together for movement between an open condition and a closed, clamping condition, the first and second clamping portions each having an upper portion, a lower portion opposite the upper portion, an outer surface, a curved interior surface opposite the outer surface, at least one barb extending radially from each curved interior surface at the upper portion, and a shroud at the lower portion that defines a recess,
    a length of flexible tubing, and
    a fluid fitting configured to receive an end of the length of flexible tubing, wherein the fluid fitting defines flange,
    wherein the barb of the first and second clamping portions engage an exterior surface of the flexible tubing and the flange of the fluid fitting is disposed in the recess of the shroud of the first and second clamping portions when the first and second clamping portions are in the closed, clamping condition to form a fluid tight connection between the fluid fitting and the flexible tubing,
    wherein when the first and second clamping portions are in the closed, clamping condition, the fluid connector has 1) a first diameter measured from a location on the curved interior surface at the upper portion of the first clamping portion that is spaced from the at least one barb of the first clamping portion to the curved interior surface of the second clamping portion, and 2) a second diameter measured from a second location on an inner surface of the shroud of the first clamping portion to an inner surface of the shroud of the second clamping portion, and 3) a third diameter measured from the outer surface of the first clamping portion to the outer surface of the second clamping portion, wherein the second diameter is greater than the first and third diameters.

10. The fluid system of claim 9, wherein the first and second clamping portions further comprise first and second clamping arms pivotally coupled to each other.

11. The fluid system of claim 9, further comprising an over center clasp mechanism configured to couple the first and second clamping portions together.

12. A method of forming a fluid tight connection between a length of flexible tubing and a fluid fitting, the method comprising:
    directing an end of the length of flexible tubing over a fluid fitting to form fluid passage communicating from the flexible tubing through the fluid fitting,
    placing a fluid connector around the end of the length of flexible tubing, moving first and second clamping portions of the fluid connector into a clamping condition onto an exterior surface of the flexible tubing, wherein each of the first and second clamping portions defines an upper portion and a lower portion opposite the upper portion, such that a recess defined by a shroud of the lower portion of each of the first and second clamping portions receives a flange defined by the fluid fitting, and engaging at least one barb extending radially from an interior surface of the first and second clamping portions at the upper portions into the exterior surface of the flexible tubing when the fluid connector is in the clamping condition to thereby form a fluid tight connection between the flexible tubing and the fluid fitting, wherein when the first and second clamping portions are in the clamping condition, the fluid connector has 1) a first diameter measured from a location on the interior surface at the upper portion of the first clamping portion that is spaced from the at least one barb of the first clamping portion to the interior surface of the second clamping portion, and 2) a second diameter measured from an inner surface of the shroud of the first clamping portion to an inner surface of the shroud of the second clamping portion, and 3) a third diameter measured from an outer surface of the first clamping portion to an outer surface of the second clamping portion, wherein the second diameter is greater than the first and third diameters.

13. The method of claim 12, wherein moving the first and second clamping portions further comprises pivoting a first clamping arm with respect to a second clamping arm about a pivot.

14. The method of claim 12, further comprising coupling the first and second clamping portions to each other with an over center clasp mechanism.

15. A fluid connector for securing a length of flexible tubing to a fluid fitting that includes a flange, the fluid connector comprising: first and second clamping portions coupled together for movement between an open condition and a closed, clamping condition for clamping an end of a length of flexible tubing to a fluid fitting, wherein each of the first and second clamping portions defines an upper portion and a lower portion opposite the upper portion, the first and second clamping portions each having a curved interior surface and at least one barb extending radially from each curved interior surface at the upper portion, the at least one barb configured to engage an exterior surface of the flexible tubing when the first and second clamping portions are in the closed, clamping condition to form a fluid tight connection between the fluid fitting and the flexible tubing, the lower portion of the first and second clamping portions each including a shroud that defines a recess, wherein the recess is configured to receive the flange of the fluid fitting, wherein when the first and second clamping portions are in the closed, clamping condition, the fluid connector 1) has a first diameter measured from a location on the curved interior surface at the upper portion of the first clamping portion that is spaced from the at least one barb of the first clamping portion to the curved interior surface of the second clamping portion, 2) has a second diameter measured from an inner surface of the shroud of the first clamping portion to an inner surface of the shroud of the second clamping portion, wherein the second diameter is greater than the first diameter, and 3) has a third diameter measured from an outer surface of the first clamping portion to an outer surface of the second clamping portion, wherein the second diameter is greater than the third diameter, and wherein the upper portions of the first and second clamping portion collectively define a first cylindrical portion of the fluid connector, and the lower portions of the first and second clamping portion collectively define a second cylindrical portion and a conical portion of the fluid connector.

16. The fluid connector of claim 15, wherein the conical portion of the fluid connecter has a fourth diameter measured from the outer surface of the first clamping portion to the outer surface of the second clamping portion, wherein the fourth diameter is greater than the first, second, and third diameters.

17. The fluid connector of claim 16, wherein the conical portion of the fluid connector is spaced between the first and second cylindrical portions of the fluid connector.

18. The fluid connector of claim 17, wherein the second cylindrical portion of the fluid connector has a fifth diameter measured from the outer surface of the first clamping portion to the outer surface of the second clamping portion, wherein the fifth diameter is greater than the first and third diameters and less than the second and fourth diameters.

19. The fluid connector of claim 18, wherein the second cylindrical portion of the fluid connector has a sixth diameter measured from the inner surface of the first clamping portion to the inner surface of the second clamping portion, wherein the sixth diameter is greater than the first and third diameters and less than the second, fourth, and fifth diameters.

* * * * *